(12) United States Patent
Tamai (10) Patent No.: US 10,603,447 B2
(45) Date of Patent: Mar. 31, 2020

(54) SAFETY APPARATUS FOR MEDICAL NEEDLES

(71) Applicant: KAWASUMI LABORATORIES, INC., Saiki-shi, Oita (JP)

(72) Inventor: Yusuke Tamai, Bungo-Ono (JP)

(73) Assignee: KAWASUMI LABORATORIES, INC., Saiki-shi, Oita (JP)

( * ) Notice: Subject to any disclaimer, the term of this patent is extended or adjusted under 35 U.S.C. 154(b) by 124 days.

(21) Appl. No.: 15/850,848

(22) Filed: Dec. 21, 2017

(65) Prior Publication Data

US 2019/0192786 A1 Jun. 27, 2019

(51) Int. Cl.
*A61M 5/32* (2006.01)
*A61M 5/158* (2006.01)
*A61M 5/162* (2006.01)
*A61M 25/06* (2006.01)

(52) U.S. Cl.
CPC .......... *A61M 5/3275* (2013.01); *A61M 5/158* (2013.01); *A61M 5/1626* (2013.01); *A61M 5/3204* (2013.01); *A61M 5/3273* (2013.01); *A61M 25/0631* (2013.01); *A61M 2005/1581* (2013.01); *A61M 2005/3226* (2013.01); *A61M 2005/3247* (2013.01)

(58) Field of Classification Search
CPC .......... A61M 2005/1581; A61M 5/158; A61M 5/3275; A61M 2005/325; A61M 2005/1583; A61M 2005/1585; A61M 2005/3247; A61M 25/0612; A61M 25/0618; A61M 25/0625; A61M 5/00; A61M 5/3273; A61M 2005/3226; A61M 25/0631; A61M 5/1626; A61M 5/3204; A61B 5/15003; A61B 5/150259; A61B 5/150389; A61B 5/150503; A61B 5/150526; A61B 5/150641; A61B 5/15074; A61B 5/153
See application file for complete search history.

(56) References Cited

U.S. PATENT DOCUMENTS

| 2005/0107748 | A1 | 5/2005 | Thorne et al. |
| 2006/0064061 | A1 | 3/2006 | Solomon et al. |
| 2007/0073222 | A1 | 3/2007 | Lilley, Jr. et al. |
| 2013/0172826 | A1* | 7/2013 | Morita ............ A61M 5/00 604/263 |

FOREIGN PATENT DOCUMENTS

| JP | 2007-511285 A | 5/2007 |
| WO | 2005/049109 A2 | 6/2005 |

\* cited by examiner

*Primary Examiner* — Brandy S Lee
(74) *Attorney, Agent, or Firm* — Sughrue Mion, PLLC (57) ABSTRACT

In a safety apparatus for medical needles, when leg portions are extended from a first folded position to a second extended position, a distal end of a needle is introduced into a space of a shield member connection hub, and a first blocking wall and a second blocking wall overlap so as to block the cross section of the space to form a double blocking wall and blocks the cross section of the space. The double blocking wall is capable of preventing the distal end of the needle from moving downward from the double blocking wall and preventing the distal end of the needle from being exposed to the outside of the apparatus.

5 Claims, 6 Drawing Sheets

SAFETY APPARATUS FOR MEDICAL NEEDLES

TECHNICAL FIELD

The present invention relates to a safety apparatus for medical needles, and particularly, relates to a safety apparatus for medical needles having a shield member (protective member) for preventing the dangerous exposure of used medical needles.

The present invention protects (shields) a bent needle (with a shape that is bent substantially 90 degrees with respect to a needle hub) constituting, for example, a port access infusion set (PAIS), and particularly, relates to improvements in a safety apparatus for medical needles where the form of the shield member (protective member) for bent needles is improved.

The "port" is a member implanted in a patient's body, and is a member constituting a system for injecting a liquid medicine such as an anticancer drug from a medical needle through this member.

BACKGROUND ART

Patent Document 1 discloses a typical prior art related to such a safety device for medical needles.

The applicant discloses in Patent Document 2 a structure that solves the problem of Patent Document 1.

Hereinafter, reference signs of the members of Patent Document 2 are bracketed by < > in the description of Patent Document 2, FIGS. 5(A), 5(B), 6(A) and 6(B) in order to avoid confusion with the reference signs of the present invention.

A second invention described in Patent Document 2 (hereinafter, the invention of Patent Document 2) has a structure in which the first and second leg portions <31, 32> are extended, the distal end <23> of the needle <21> is introduced into the space <40S> of the shield member connection hub <40H'> and further, the lower wall <42B'> of the connection hub <40H'> shifts its position so as to block the cross section of the opening portion <40O'> of the connection hub <40H'>.

FIGS. 35(A) and 35(B) of Patent Document 2 discloses a condition (the second state) where the cross section of the opening portion <40O'> of the connection hub <40H'> (or the neighborhood of the opening portion <40O'>) is blocked by the lower wall <42B'> of the slide member <42'> and the distal end <23> of the needle <21> is accommodated in the space <40S> to be protected (shielded).

Document 1 JP2007-511285A (claims, FIGS. 1-7 and FIGS. 16-28; patent family U.S. Pat. No. 7,351,230)

Document 2 US2013/0172826A1, FIGS. 24-53 and paragraphs [0314]-[0438]

Figure 5A:
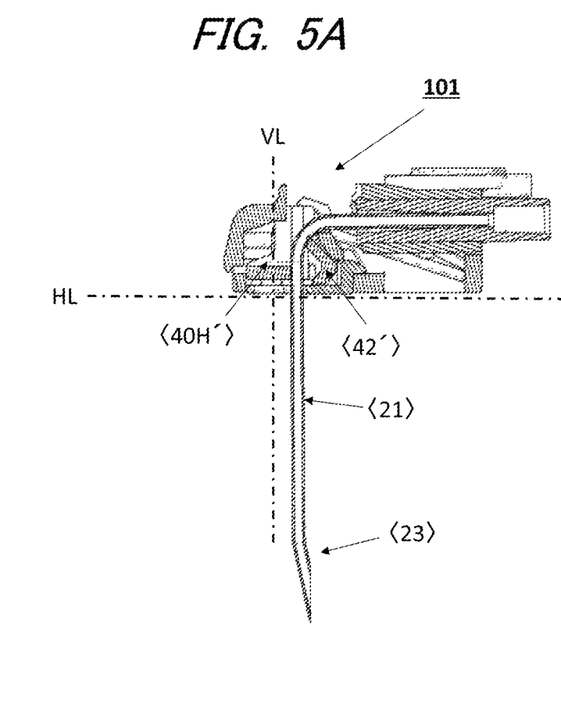
FIGS. 5A and 5B are longitudinal cross-sectional views (in the direction of the horizontal axial line HL) of a conventional medical needle safety apparatus 101 in a first state, FIG. 5A being a longitudinal view of the entire structure, and FIG. 5B being a partially enlarged view of FIG. 5A.
Figure 5B:
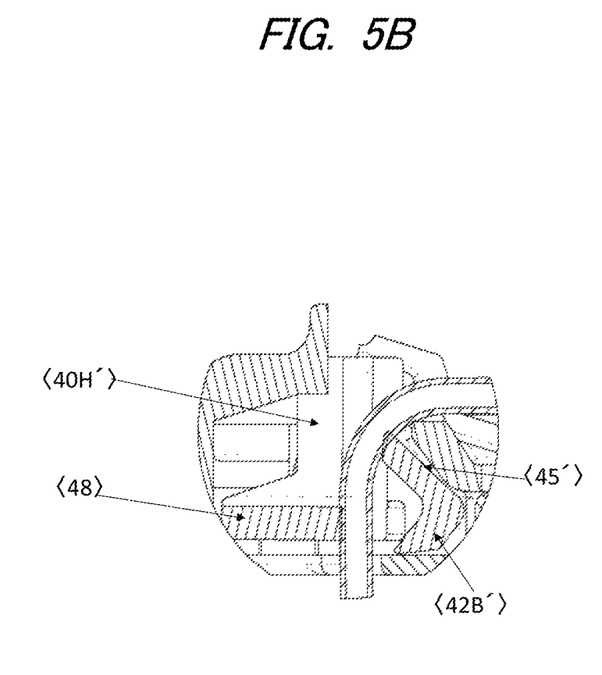
Figure 6A:
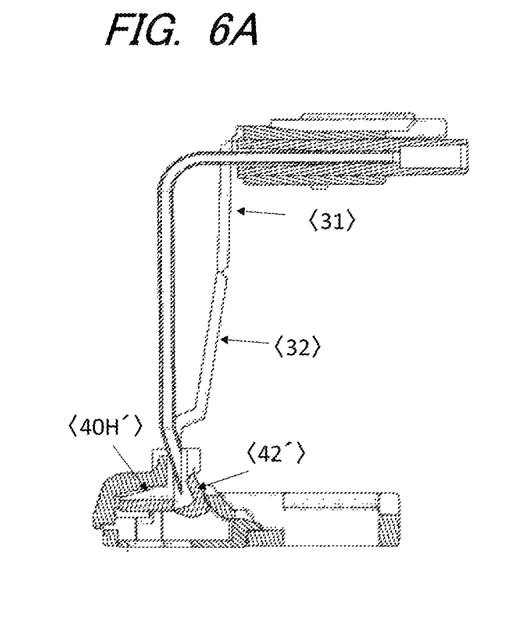
FIGS. 6A and 6B are longitudinal cross-sectional views (in the direction of the horizontal axial line HL) of the conventional medical needle safety apparatus 101 in a second state, FIG. 6A being a longitudinal view of the entire structure, and FIG. 6B being a partially enlarged view of FIG. 6A.
Figure 6B:
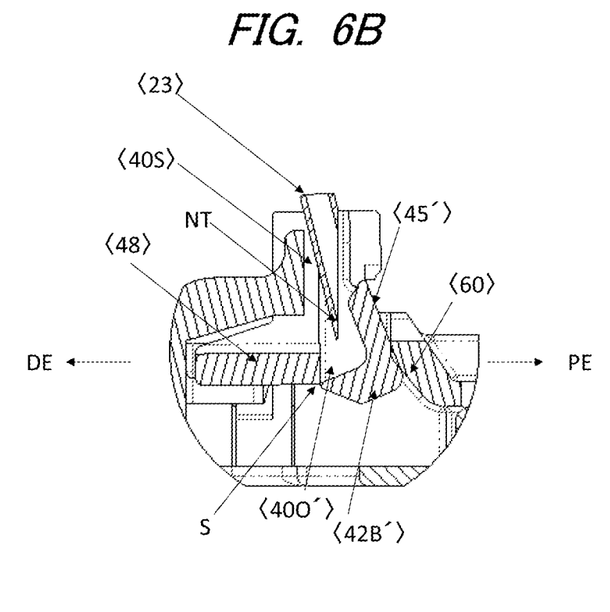

However, since the invention of Patent Document 2 (medical needle safety apparatus 101) has a structure in which the shield member connection hub <40H'> is inserted in the fixing member connection hub <50H'> (see FIGS. 29(A) and 29(B) of Patent Document 2 corresponding to FIGS. 5A and 5B of the present application], when transition is made from the first state to the second state (FIGS. 35(A) and 35(B) of Patent Document 2), the following problem is pointed out:

In practice, as shown in FIGS. 6A and 6B, there are cases where the upper side of the distal end DE side of the lower wall <42B'> of the slide member <42'> is caught on the proximal end PE side at a lower side of the shield member first latching portion <48> and the cross section of the space <40S> of the shield member connection hub <40H'>, the opening portion <40O'> (or the neighborhood of the opening portion <40O'>) cannot be blocked.

In the above cases, the contact portion S of the upper side of the distal end DE side of the lower wall <421T> and the lower side of the proximal end PE side of the shield member first latching portion <48> is weak in the penetration resistance of the distal end <23> of the needle <21> because the wall is thin.

SUMMARY OF THE INVENTION

An object of the present invention is to provide a safety apparatus for medical needles that fully closes a cross section of a space in a shield member connection hub so that a distal end (pointed end) of a needle is not exposed to the outside.

According to an aspect of the present invention, a safety apparatus for medical needles is provided. The safety apparatus has a needle member, a shield member and a fixing member. The needle member includes a needle having a distal end. The shield member includes a shield member connection hub and a leg portion. The fixing member includes a fixing member connection hub. The shield member connection hub includes a first blocking wall and a second blocking wall. The shield member connection hub is disposed inside the fixing member connection hub. When the leg portion is extended from a first folded position to a second extended position, the distal end of the needle is introduced into a space in the shield member connection hub, and the first blocking wall and the second blocking wall overlap so as to block a cross section of the space to form a double blocking wall. The double blocking wall is formed to prevent the distal end of the needle from moving downward from the double blocking wall.

According to another aspect of the present invention, the shield member connection hub may include a slide member provided at a proximal end of the shield member connection hub, and the first blocking wall may be provided on the slide member.

According to another aspect of the present invention, the second blocking wall may be provided at a lower portion of the shield member connection hub.

According to the present invention, when the leg portions are extended from the first folded position to the second extended position, the distal end of the needle is introduced into the space in the shield member connection, and the first blocking wall and the second blocking wall overlap so as to block the cross section of the space to form the double blocking wall and blocks the cross section of the space.

Accordingly, the double blocking wall is capable of preventing the distal end of the needle from moving downward from the double blocking wall and preventing the distal end of the needle from being exposed to the outside.

PREFERRED EMBODIMENTS OF THE INVENTION

Hereinafter, the present invention will be described in detail with reference to the drawings.

The following definitions are made for a clear explanation of the present invention.

Figure 1A:
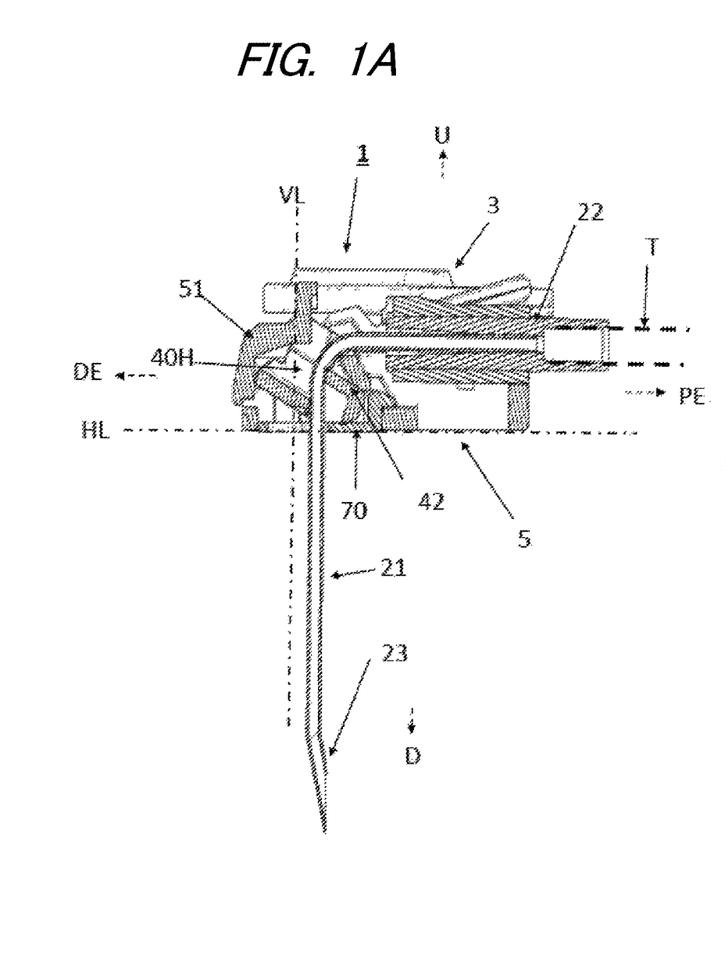
FIGS. 1A and 1B are longitudinal cross-sectional views (in the direction of a horizontal axial line HL) of a medical needle safety apparatus 1 of the present invention in a first state, FIG. 1A being a longitudinal cross-sectional view of the entire structure, and FIG. 1B being a partially enlarged view of FIG. 1A.

(i) A "first state" in a medical needle safety apparatus 1 of the present invention, means a state where first and second leg portions (31, 32) of a shield member 3 are in a completely folded position, for example, as shown in FIG. 1A. In other words, it means the following state: While the first and second leg portions (31, 32) are completely folded, a needle 21 extends downward to be in a state of being subjected to use for an operation such as transfusion or being in use, and further, a distal end 23 is unprotected (unshielded).

Figure 2A:
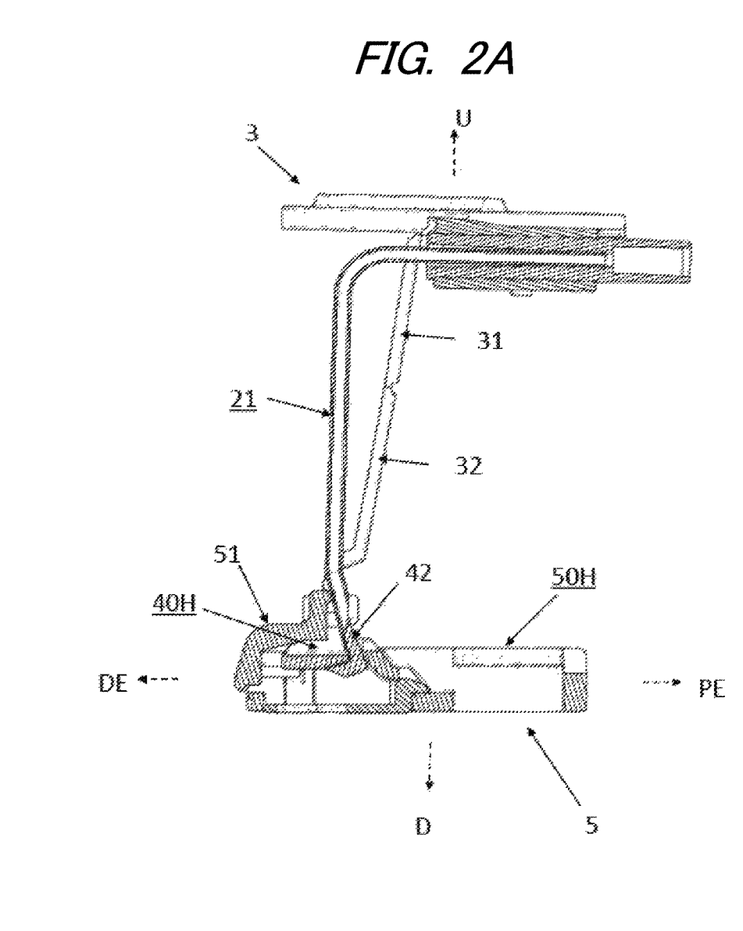
FIGS. 2A and 2B are longitudinal cross-sectional views (in the direction of the horizontal axial line HL) of the medical needle safety apparatus 1 of the present invention a second state, FIG. 2A being a longitudinal cross-sectional view of the entire structure, and FIG. 2B being a partially enlarged view of FIG. 2A.

(ii) Likewise, a "second state" means a state where the first and second leg portions (31, 32) of the shield member 3 are in a completely extended position, for example, as shown in FIG. 2A. In other words, it means a state where the distal end 23 of the needle 21 is confined in the medical needle safety apparatus 1 to be protected (shielded) in a state where the use (puncture) of the needle is finished and the first and second leg portions (31, 32) are in a completely extended state.

(iii) A "transition state" means a state where transition from the "first state" to the "second state" is under way.

(iv) A "transition start state" means an initial state where the transition from the "first state" to the "second state" is started.

(v) A "transition end state" means a state just before the end of the transition from the "first state" to the "second state".

Figure 1B:
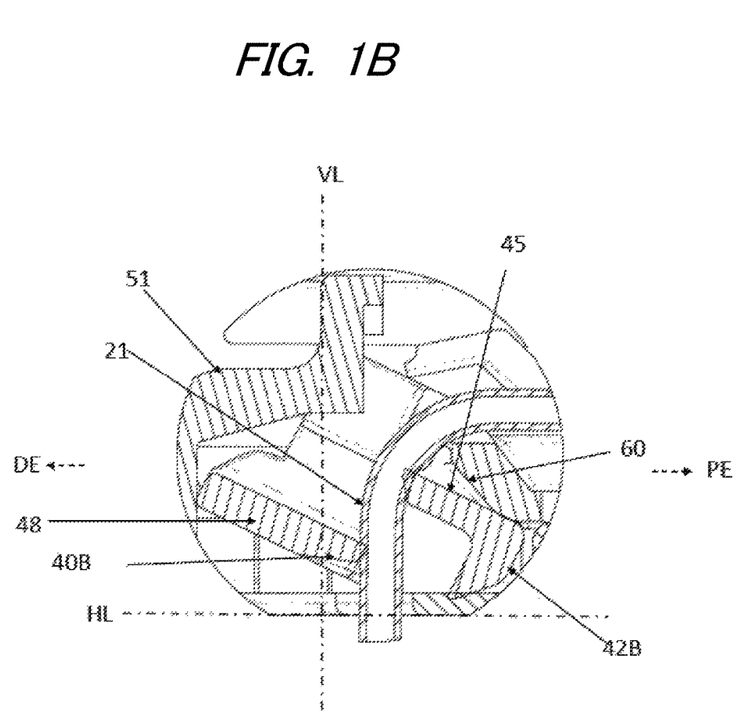

(vi) In the present invention, a "proximal end PE (side or direction)" means an end portion of a tube T side to be connected to a needle hub 22 as shown in FIGS. 1A and 1B.

(vii) A "distal end DE (side or direction)" means an end portion of a side where the needle 21 is fit as shown in FIGS. 1A and 1B.

(viii) A "horizontal axial line HL (direction)" means a direction extending, for example, in the direction of the length of the tubular needle hub 22 as shown in FIGS. 1A and 1B (see the broken lines in the drawings).

(iix) A "vertical axial line VL (direction)" means a direction in which, for example, the part that is bent in the middle of the needle 21 vertically extends downward in the direction of the length as shown in FIGS. 1A and 1B (see the broken lines of the drawings).

(ix) A "first side portion S1 (side or direction)" means a direction of the end portion on the front side of the drawing sheet in FIGS. 1A and 1B and on the right side when viewed from the distal end DE side to the proximal end PE side as shown in FIGS. 3A to 4B.

(x) A "second side portion S2 (side or direction)" means a direction of the end portion on the back side of the drawing sheet in FIGS. 1A and 1B and on the left side when viewed from the distal end DE side to the proximal end PE side as shown in FIGS. 3A to 4B.

(xi) "Upward U (side or direction)" means the upward U side of the drawing sheet as shown in FIG. 1A.

(xii) "Downward D (side or direction)" means the downward D side of the drawing sheet as shown in FIG. 1A.

Medical Needle Safety Apparatus 1

The medical needle safety apparatus 1 (hereinafter, sometimes referred to merely as "apparatus 1") of the present invention will be described below with reference to the drawings.

The medical needle safety apparatus 1 of the present invention has, as shown in FIGS. 1A and 1B, a needle member 2, the shield member 3 and a fixing member 5.

Since the detailed forms and functions of the needle member 2 and the fixing member 5 are substantially the same as the description (the second invention, FIGS. 24 to 53, and the description of the invention corresponding to the figures; see also the first invention, FIGS. 1 to 23 and the description of the invention corresponding to the figures if necessary) of US2013/0172826A1 (Patent Document 2) that the applicant has already filed in the United States, the description of these members and the illustration of the figures are minimized, and the shield member 3 which is a feature of the present invention will mainly be described.

A feature of the present invention is as follows: When the leg portions (31, 32) are extended from a first folded position to a second extended position, the distal end 23 of the needle 21 is introduced into a space 40S of a shield member connection hub 40H, and a first blocking wall 42B and a second blocking wall 40B overlap so as to block the cross section of the space 40S to form a double blocking wall DW and blocks the cross section of the space 40S. The double blocking wall DW is formed to prevent the distal end 23 of the needle 21 from moving downward D from the double blocking wall DW and preventing the distal end 23 of the needle 21 from being exposed to the outside.

Hereinafter, an embodiment of the present invention will be described in detail.

In the embodiment of the present invention, the first blocking wall is, for example, a lower wall 42B of a slide member 42, and the second blocking wall is, for example, a lower wall 40B newly provided on the downward D side of the connection hub 40H of the shield member 3.

The slide member 42 has a so-called substantially L-shaped form. The "long member" of the "L" shape is connected to the proximal end PE side of the distal end side shield member connection hub 40H through a hinge 44H.

The "long member" slides along a slide wall 60 of the fixing member 5 and therefore will be referred to as a "slide wall 45". The "short member" is situated downward from the slide wall 45 and therefore will be referred to as the lower wall 42B.

The lower wall 42B functions as the "first blocking wall".

The slide wall 45 and the lower wall 42B of the slide member 42, which slide as described above with a hinge 44 as the starting point and move to the upper side U, are sometimes referred to as "rotary members".

The lower wall 40B as the second blocking wall is formed at the portion of the shield member connection hub 40H facing downward D. Describing further in detail, it is formed between the portions of a shield member third latching portions 47 of the first side portion S1 side and the second side portion S2 side on the downward side D (compared with FIG. 6B, the position of the opening portion <40O'>).

The first blocking wall (lower wall) 42B overlaps the second blocking wall (lower wall) 40B on the side of the second blocking wall (lower wall) 40B that faces downward D, thereby forming the double blocking wall DW to block the cross section of the space 40S of the shield member connection hub 40H.

Figure 2B:
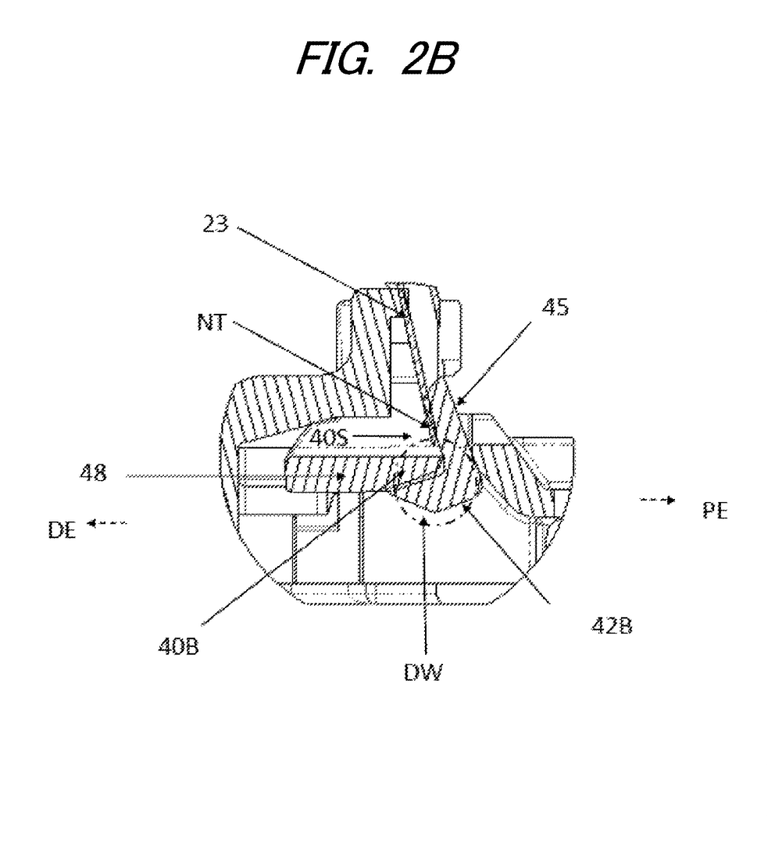
Figure 3A:
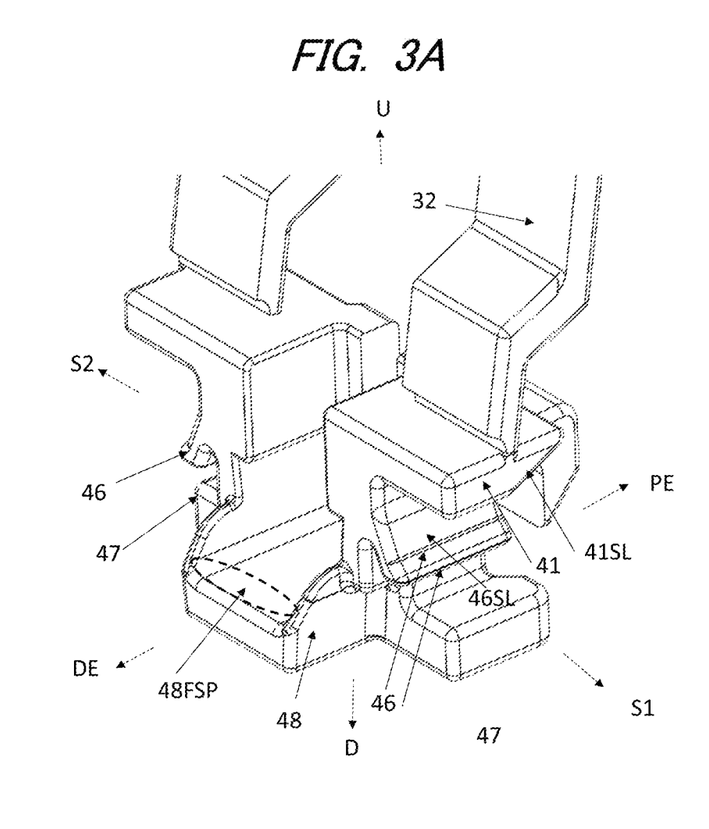
FIGS. 3A and 3B are partially enlarged perspective views of the neighborhood of a connection hub 40H of the medical needle safety apparatus 1 of the present invention, FIG. 3A being a perspective view viewed in a direction from an upper side U, a distal end DE to a first side portion S1, and FIG. 3B being a perspective view viewed in a direction from a downward side D, a proximal end PE to the first side portion S1.
Figure 3B:
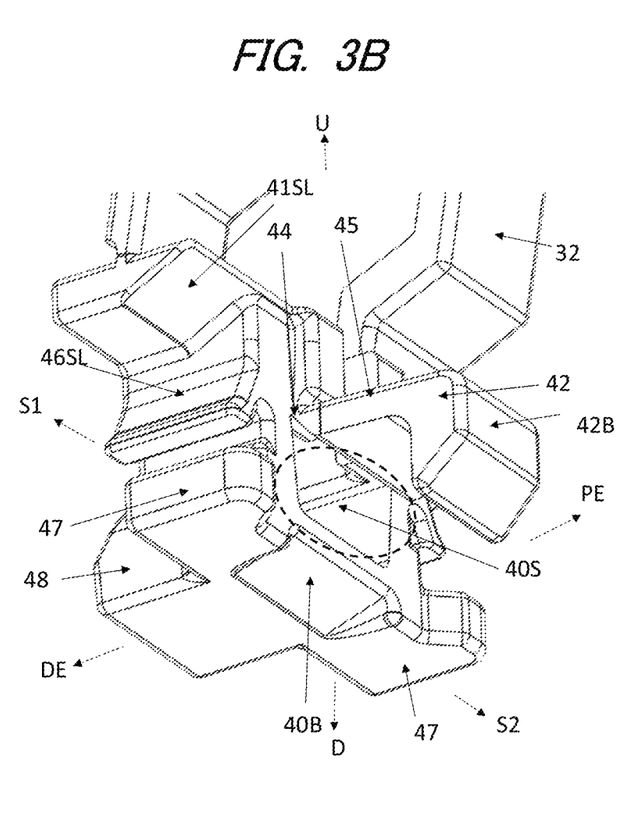
Figure 4A:
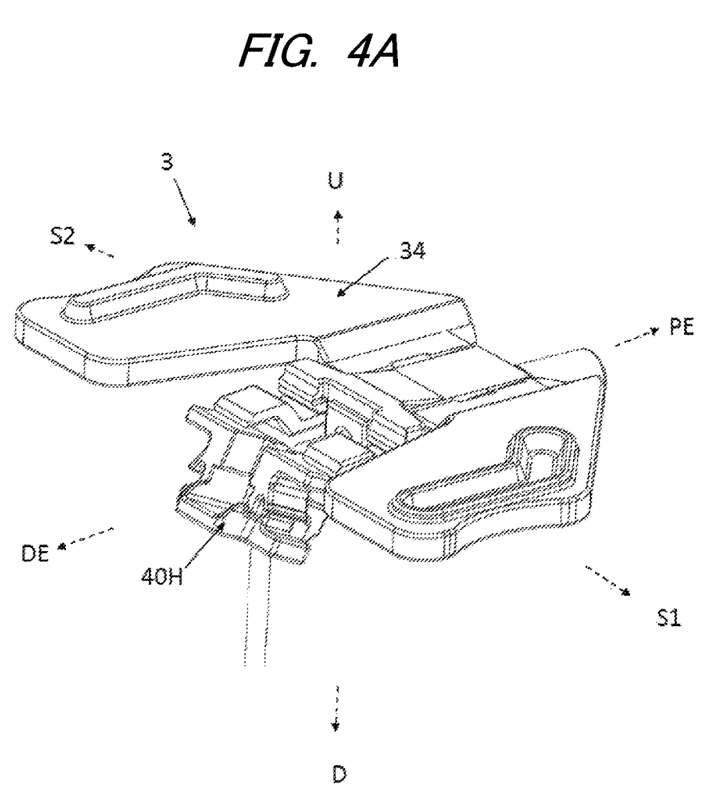
FIGS. 4A and 4B are overall perspective views of a needle member 2 and a shield member 3 of the medical needle safety apparatus 1 of the present invention in the first state, FIG. 4A being a perspective view viewed in the direction from the upper side U, the distal end DE to the first side portion S1, and FIG. 4B being a perspective view viewed in the direction from the downward side D, the proximal end PE to the first side portion S1.
Figure 4B:
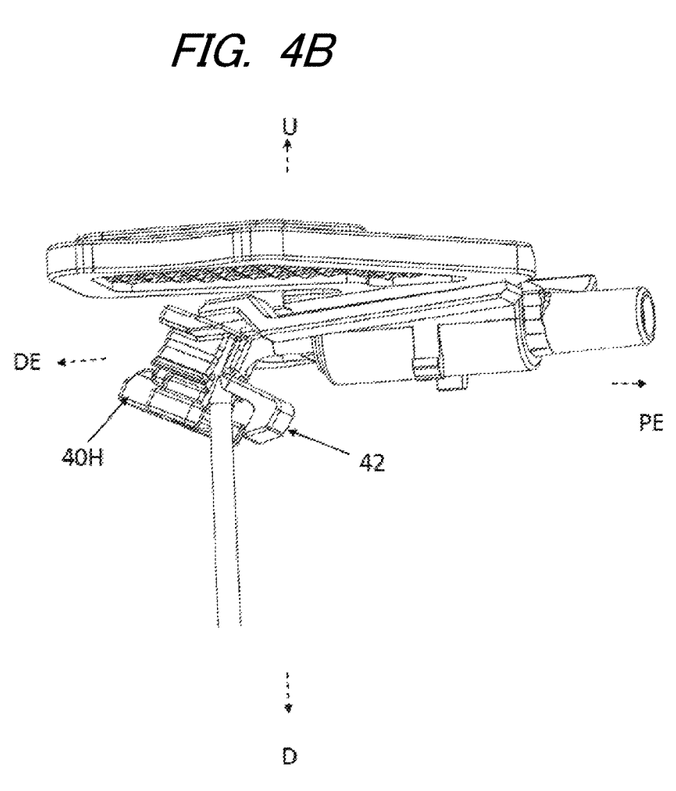

The "the first blocking wall 42B overlaps the second blocking wall 40B on the side of the second blocking wall 40B that faces downward D" may be as follows:

As shown in FIG. 2B, a slight gap (space) may be present between the upper U side (top surface) of the first blocking wall 42B and the downward D side (bottom surface) of the second blocking wall 40B, or (although dare not illustrate it), adjustment may be made so that the upper U side (top surface) of the first blocking wall 42B and the downward D side (bottom surface) of the second blocking wall 40B are "completely", "mostly" or "partly" in contact with each other.

Other differences of the present invention from the second invention described in Patent Document 2 are as follows:

(A) In order to reduce the interference of the components of the shield member connection hub 40H and the like with the components of a fixing member connection hub 50H when the leg portions (31, 32) are extended from the first folded position to the second extended position, an "interference reducing portion" is formed as follows:

(A1) The wall of the upper U side of the distal end DE side of the shield member first latching portion 48 is shaved to form a notch space 48FSP (in order to reduce the interference with the cover <51'>), and (A2) the wall of the proximal end PE side of the side portions S1 and S2 side of an upper connection portion 41 connecting the lower portions of the leg portions (31, 32) and the portion of the shield member connection hub 40H on the upper side U is removed to form an inclined surface 41SL (in order to reduce the interference with the first upper wall <61>).

(B) In order that return from the second state to the first state does not occur, a shield member second latching portion 46 is formed in a so-called "wing" form and provided so as to largely protrude in the direction of the downward side D and in the direction of the side portion S1 (S2). Describing further in detail, an inclined surface 46SL is formed so as to warp in the direction of the first side portion S1 (the second side portion S2). Because of the inclined surface 46SL, the shield member second latching portion 46 readily moves toward the upper side U, and because of the wing form, it functions as a strong return-prevention hook for the first upper wall <61> of the fixing member connection hub 50H.

(C) The volume of the opening portion 40S of the shield member connection hub 40H is made large (wide) (particularly, in the direction from the distal end DE side to the proximal end PE) so that the first shielding wall and the second shielding wall readily overlap on the downward D side of the space 40S.

Assembling to First State (Assembling of Needle Member 2, Shield Member 3 and Fixing Member 5)

Hereinafter, differences from the invention of Patent Document 2 will be described.

While in the invention of Patent Document 2, the shield member connection hub <40H> is disposed parallel to the vertical axial line VL and vertical to the horizontal axial line HL as shown in FIGS. 5A and 5B, in the illustration of FIGS. 1A and 1B of the present invention, since the proximal end PE side of the newly formed second blocking wall (lower wall 40B) is pushed to the distal end DE side by the outer periphery of the needle 21, the shield member connection hub 40H is disposed so as to be inclined (at an angle) with respect to the vertical axial line VL and the horizontal axial line HL.

In the invention of the present application, since the second blocking wall is not limited to the form and the position of formation of the lower wall 40B, the shield member connection hub 40H may be disposed in the fixing member 5 (the fixing member connection hub 50H) according to the form and the position of formation of the second blocking wall.

Protection (Shielding) of Distal End 23 of Needle 21

Hereinafter, differences from the invention of Patent Document 2 will be mainly described.

(1) "Transition Start State"

When the needle 21 is lifted up toward the upper side U of the vertical axial line VL from a first position, along therewith, the first and second leg portions (31, 32) start to extend toward the upper side U.

Along therewith, the needle 21 and the shield member connection hub 40H move toward the upper side U.

The slide wall 45 of the slide member 42 starts to move (slide) from the proximal end PE side to the distal end DE side along the slide wall (inclined wall) 60 of the fixing member connection hub 50H, and moves toward the upper side U. The first blocking wall (the lower wall 42B) of the slide member 42 also moves toward the upper side U following the slide wall 45.

The second blocking wall (the lower wall 40B) starts to move from the distal end DE side to the proximal end PE side, and moves to toward the upper side U.

(2) "Transition End State"

The first and second leg portions (31, 32) moves to fully extend toward the upper side U as illustrated in FIG. 2A. The second latching portion 46 moves to climb over a first upper wall 61 along the inclined surface 46SL.

The first blocking wall (the lower wall 42B) of the slide member 42 overlaps the second blocking wall (the lower wall 40B) on the side of the second blocking wall (the lower wall 40B) that faces downward D, and shifts its position so as to close the cross section of the downward D side of the space 40S.

(3) Second State

As shown in FIG. 2A, the first and second leg portions (31, 32) completely extend toward the upper side U.

The portion of the second latching portion 46 of the shield member 3 facing downward D is latched to the upper portion (top surface) of the first upper wall 61. The second latching portion 46 functions as a strong return-prevention hook.

The first blocking wall (the lower wall 42B) of the slide member 42 with which the second blocking wall (the lower wall 40B) overlaps in (the downward D side of) the space 40S functions as the double blocking wall DW to block the cross section of the space 40S.

The distal end 23 of the needle 21 is accommodated in the space 40S to be protected (shielded).

The double blocking wall DW functions as a strong protective wall that prevents the distal end 23 of the needle 21 from moving downward D from the double blocking wall DW and from being exposed to the outside of the apparatus 1.

OTHER EMBODIMENTS

In the present invention, the forms and the positions of disposition of the first blocking wall, the second blocking wall and the interference reducing portion are not limited to the ones shown in the above description and figures as long as the object of the present invention can be achieved.

For example, in the illustration of the state of FIG. 2B, the first blocking wall (the lower wall 42B) has a form tapered from the distal end DE side toward the upper side U and the second blocking wall (the lower wall 40B) has a form tapered from the proximal end PE side toward the upper side U, however, the forms and the positions of disposition are not limited to the ones illustrated in the drawings in so far as the object of the present invention can be achieved.

Moreover, in the illustration of the state of FIG. 2B, although the pointed end NT of the distal end 23 of the needle 21 appears to be in contact with the slide wall 45 of the slide member 42 to be fixed, the pointed end NT may be adjusted so as to be situated toward an upper side U than the double blocking wall DW. Even if the pointed end NT comes into contact with the double blocking wall DW, the double blocking wall DW serves as a strong protective wall so that the distal end 23 of the needle 21 can be prevented from being exposed to the outside of the apparatus 1.

What is claimed is:

1. A safety apparatus for medical needles, the safety apparatus comprising a needle member, a shield member and a fixing member,
   wherein the needle member comprises a needle having a distal end,
   wherein the fixing member comprises a fixing member connection hub,
   wherein the shield member comprises a shield member connection hub disposed inside the fixing member connection hub and a leg portion connected to the shield member connection hub,
   wherein the shield member connection hub comprises a first blocking wall and a second blocking wall,
   wherein, when the leg portion is in a folded position, the first blocking wall and the second blocking wall are separated from each other, and
   wherein, with the leg portion extending from the folded position to an extended position,
   the distal end of the needle is introduced into a space in the shield member connection hub,
   the first blocking wall and the second blocking wall move relative to each other so as to overlap each other directly below the distal end of the needle to form a double blocking wall,
   the double blocking wall being formed to prevent the distal end of the needle from moving downward from the double blocking wall.

2. The safety apparatus according to claim 1, wherein the shield member connection hub comprises a slide member provided at a proximal end of the shield member connection hub, and
   the first blocking wall is provided on the slide member.

3. The safety apparatus according to claim 1, wherein the second blocking wall is provided at a lower portion of the shield member connection hub.

4. The safety apparatus according to claim 1, wherein the first blocking wall is rotatable relative to the second blocking wall.

5. The safety apparatus according to claim 1, wherein, when the leg portion is folded from the extended position to the folded position, the first blocking wall and the second blocking wall are separated from each other to allow the distal end of the needle to move downward through the space between the first blocking wall and the second blocking wall.

* * * * *